(12) United States Patent
White et al.

(10) Patent No.: US 11,439,511 B2
(45) Date of Patent: Sep. 13, 2022

(54) ORTHOPAEDIC KNEE IMPLANT SYSTEM WITH CONTROLLED STIFFNESS

(71) Applicant: DePuy Ireland Unlimited Company, Ringaskiddy (IE)

(72) Inventors: Stephen E. White, Fort Wayne, IN (US); William J. Maloney, Palo Alto, CA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

(21) Appl. No.: 16/863,112

(22) Filed: Apr. 30, 2020

(65) Prior Publication Data

US 2021/0338440 A1    Nov. 4, 2021

(51) Int. Cl.
*A61F 2/38* (2006.01)
*A61F 2/30* (2006.01)

(52) U.S. Cl.
CPC .... *A61F 2/389* (2013.01); *A61F 2002/30014* (2013.01); *A61F 2002/3093* (2013.01)

(58) Field of Classification Search
CPC ...................................................... A61F 2/389
See application file for complete search history.

(56) References Cited

U.S. PATENT DOCUMENTS

| | | | |
|---|---|---|---|
| 7,578,851 B2 | 8/2009 | Dong et al. | |
| 8,382,845 B2 | 2/2013 | Metzger et al. | |
| 8,430,930 B2 | 4/2013 | Hunt | |
| 8,747,479 B2 | 6/2014 | McShane et al. | |
| 9,132,013 B2 | 9/2015 | Armacost et al. | |
| 9,211,190 B2 | 12/2015 | Salyer | |
| 9,517,136 B2 | 12/2016 | Sanchez et al. | |
| 9,561,354 B2 | 2/2017 | Nebosky et al. | |
| 9,925,363 B2 | 3/2018 | Maganoli | |
| 9,956,048 B2 | 5/2018 | Bojarski et al. | |
| 2005/0055101 A1* | 3/2005 | Sifneos | A61F 2/389 623/20.32 |
| 2007/0179627 A1 | 8/2007 | Gustilo et al. | |
| 2008/0027556 A1 | 1/2008 | Metzger | |
| 2009/0125115 A1* | 5/2009 | Popoola | A61F 2/38 623/20.14 |
| 2009/0130167 A1 | 5/2009 | Shelton et al. | |
| 2010/0168857 A1* | 7/2010 | Hatch | A61F 2/389 623/14.12 |

(Continued)

FOREIGN PATENT DOCUMENTS

| | | |
|---|---|---|
| EP | 2365792 A1 | 9/2011 |
| WO | 2010045537 A1 | 4/2010 |
| WO | 2017098316 A1 | 6/2017 |

OTHER PUBLICATIONS

International Search Report for application No. PCT/EP2021/061369, dated Jul. 9, 2021, 5 pages.

(Continued)

*Primary Examiner* — Javier G Blanco
(74) *Attorney, Agent, or Firm* — Barnes & Thornburg LLP (57) ABSTRACT

A tibial implant includes one or more stiffness-modifying features to reduce the stiffness of one or more sections of the tibial implant. The stiffness-modifying features may include slots, recesses, or passageways defined in various locations of the tibial implant to selectively reduce the stiffness of a tibial insert and/or tibial base of the tibial implant.

7 Claims, 5 Drawing Sheets

(56) References Cited

U.S. PATENT DOCUMENTS

| | | |
|---|---|---|
| 2011/0046735 A1* | 2/2011 | Metzger ................ A61F 2/3868 623/14.12 |
| 2011/0202140 A1 | 8/2011 | Turner et al. |
| 2012/0277881 A1* | 11/2012 | McShane ................ A61F 2/389 623/20.31 |
| 2015/0051539 A1 | 2/2015 | Lin |
| 2016/0235955 A1* | 8/2016 | Magagnoli ............. A61F 2/389 |
| 2017/0165076 A1 | 6/2017 | Maganoli |

OTHER PUBLICATIONS

Zimmer NexGen Trabecular Metal Monoblock Tibial Components Surgical Technique Addendum, CR and LPS Articular Surface Geometry with a Trabecular Metal Base Plate, 2012, 7 pages, 97-7255-134-00 Rev. 1 3ML.

Zimmer Trabecular Metal Monoblock Tibial Components, Setting a New Gold Standard in Cementless TKA, 2007, 4 pages, 97-7255-133-00 5ML.

\* cited by examiner

ORTHOPAEDIC KNEE IMPLANT SYSTEM WITH CONTROLLED STIFFNESS

TECHNICAL FIELD

The present invention relates to orthopaedic systems, and, more particularly, to orthopaedic systems for performing knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial insert in cases wherein it is desirable to limit the movement of the knee prosthesis, such as when significant soft tissue damage or loss is present. Alternatively, the knee prosthesis may include a "mobile" tibial insert in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior-stabilized knee prosthesis may be used to provide additional support and/or control at later degrees of flexion. Alternatively, if the posterior cruciate ligament is intact, a cruciate-retaining knee prosthesis may be used.

One consideration of joint arthroplasty is bone growth around or near the implanted knee prosthesis. Bone tissue growth and resorption is directly related to the loading experienced by the bone tissue. This phenomenon, which is referred to as Wolfe's law, results in abnormal growth of bone tissue that experiences abnormal loading. Abnormal growth of the bone tissue may be, for example, a result of stress shielding where the bone density is considerably lower in a region adjacent to an implant. The bone density lowers due to the implant experiencing the brunt of the load in the region, i.e., the implant shields the bone from stress, resulting in reduced density. The reduced density can weaken the bone tissue in the region to a point where there is an increased risk of further dysfunction or damage, such as fracturing.

One particular issue with orthopaedic implants in view of Wolfe's law is the geometric and material requirements. Orthopaedic implants, generally, comprise materials other than bone tissue, such as various metals and/or polymers. The materials may be chosen to match the material properties of native bone tissue as closely as possible, but a perfect match is difficult to achieve. Further, the shape of the implant must match the shape of the portion of bone that is resected to allow implantation. This is particularly important with regards to thicknesses of the implant in various regions, which may have a thickness that results in excessive stiffness in order to properly fill the joint space. These two issues can contribute to abnormal bone loading.

SUMMARY

The present invention provides an orthopaedic knee system including one or more components with a modified stiffness to simulate natural load distribution on bone tissue and reduce the risk of, for example, bone density loss due to stress shielding and other bone tissue abnormalities.

According to an aspect of the present disclosure, a tibial insert includes a medial articular surface, a lateral articular surface, and a central body formed between the medial articular surface and the lateral articular surface, wherein the central body includes a stiffness-modifying feature.

In some embodiments, the stiffness-modifying feature may include a groove defined in the central body. Additionally, in some embodiments, a therapeutic agent disposed in the groove. The groove may be linear or curved when the tibial insert is viewed in a transverse plane. In some embodiments, the groove may extend from an anterior side of the tibial insert to a posterior side of the tibial insert. For example, the groove may extend linearly from an anterior side of the tibial insert to a posterior side of the tibial insert. Alternatively, the groove may curve from an anterior side of the tibial insert to a posterior side of the tibial insert.

In some embodiments, the tibial insert may further includes a post extending superiorly from the central body. In such embodiments, the stiffness-modifying feature may be embodied as a first stiffness-modifying feature defined in the central body medially of the post and a second stiffness-modifying feature defined in the central body laterally of the post. In some embodiments, each of the first and second stiffness-modifying features include is a groove defined in the central body. Additionally, in some embodiments, at least one of the grooves is a linear when the tibial insert is viewed in a transverse plane. Additionally or alternatively, at least one of the grooves may be a curved when the tibial insert is viewed in a transverse plane.

In some embodiments, the central body may include an inner wall that defines the stiffness-modifying feature. For example, the inner wall may define a groove in the central body, such as a curved or linear groove. Additionally, in some embodiments, stiffness-modifying feature may include a passageway defined in the central body. The passageway may be embodied as a blind passageway having an opening on an anterior side of the central body or a posterior side of the central body. Alternatively, the passageway extends through the central body and may include a first opening on an anterior side of the central body and a second opening on a posterior side of the central body. In some embodiments, the tibial insert may include a therapeutic agent disposed in the passageway. Additionally, in some embodiments, the tibial insert may include a groove defined on a top surface of the central body, and the groove is in fluid communication with the passageway. The groove may define a pair of tabs of the central body, which may be movable into the passageway in response to a force applied to the tabs. A therapeutic agent may be disposed in the passageway, and the tabs may cause a release of the therapeutic agent from the passageway in response to the force. Further, in some embodiments, the tibial insert may include a pair of openings defined on an anterior side of the central body. In such embodiments, each of the openings may be configured to receive a tensioner operable to move the tabs of the central body to cause the release of the therapeutic agent form the passageway.

According to another aspect, a tibial prosthesis for implantation into a surgically-prepared tibia of a patient may include a platform and a rail. The platform may include a top surface configured to receive a tibial insert. The rail may be coupled to a periphery of the platform. The rail may also include a stiffness-modifying feature.

In some embodiments, the stiffness-modifying feature is a slot defined in the rail. For example, the stiffness-modifying feature may be embodied as a rail section having a height, relative to the top surface of the platform, that is less than a height of an adjacent rail section. Additionally or alternatively, the stiffness-modifying feature may include a recess defined in the top surface of the platform. In some embodiments, the tibial prosthesis may include a therapeutic agent disposed in the recess.

Accordingly to yet another aspect, a tibial prosthesis for implantation into a surgically-prepared tibia of a patient may include a platform having a bottom surface and a keel extending inferiorly from the bottom surface of the platform. The keel may include a stiffness-modifying feature. In some embodiments, the stiffness-modifying feature may be embodied as an undercut defined in the keel adjacent to the bottom surface of the platform.

According to a further aspect, a tibial prosthesis for implantation into a surgically-prepared tibia of a patient may include a polymer platform and a keel. The polymer platform may have a superior surface and an inferior surface opposite the superior surface, and the keel may extend from the inferior surface of the polymer platform. The polymer platform includes a plurality of stiffness-modifying features defined in the inferior surface. In some embodiments, the one or more of the plurality of stiffness-modifying features may be embodied as a slot defined in the inferior surface of the polymer platform. For example, the slot(s) may be defined in the inferior surface of the polymer platform in an anterior-posterior direction. Additionally or alternatively, the inferior surface of the polymer platform may include a porous ingrowth surface and at least two slots of the plurality of slots may intersect each other.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1A:
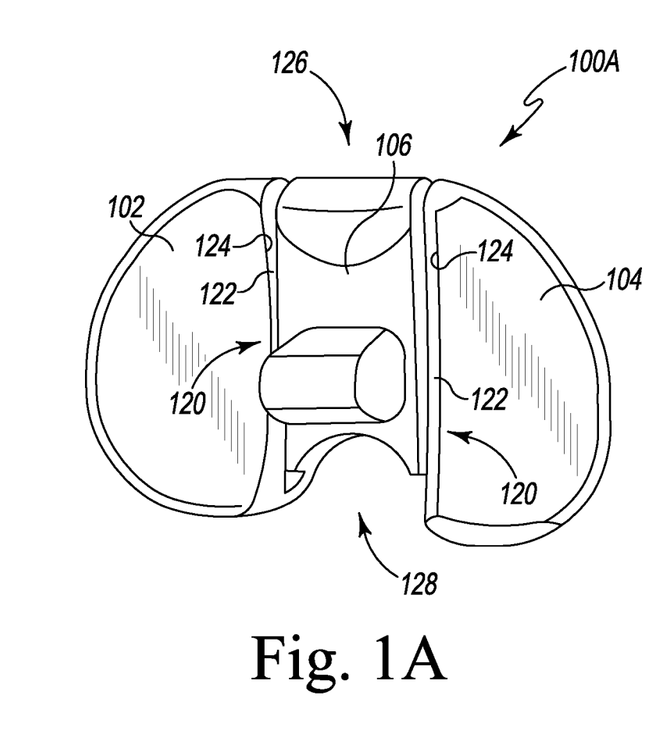
FIG. 1A is a superior plan view of a tibial insert including stress-modifying features defined in a top surface of a body of the tibial insert.
Figure 1B:
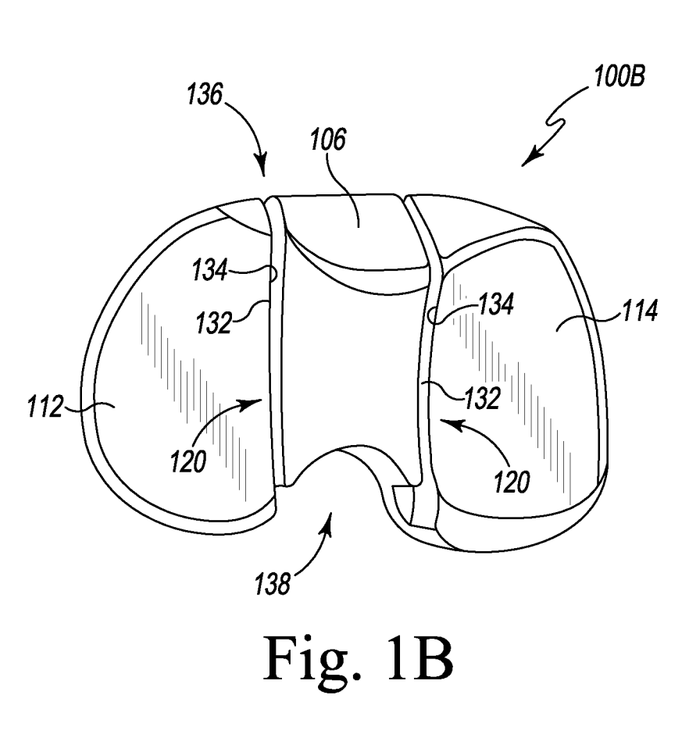
FIG. 1B is a superior plan view of another tibial insert including stress-modifying features defined in a top surface of a body of the tibial insert.

Referring now to the drawings, and more particularly to FIGS. 1A and 1B, illustrative embodiments of tibial inserts 100A, 100B provided in accordance with the present disclosure are illustrated. The tibial inserts 100A, 100B may be similar in shape, with the primary difference being that the tibial insert 100A includes a post 108, while the tibial insert 100B does not. As illustrated, the tibial inserts 100A, 100B are shaped for use in an orthopaedic system, which may also include a femoral component that bears on articular surfaces of the tibial inserts 100A, 100B. For example, the tibial insert 100A includes a medial articular surface 102, a lateral articular surface 104, and a central body 106 defined between the medial and lateral articular surfaces 102, 104. The post 108 extends upwardly (i.e., superiorly) from the central body 106. Similarly, the tibial insert 100B includes a medial articular surface 112, a lateral articular surface 114, and a central body 116 defined between the medial and lateral articular surfaces 102, 104. As discussed above, the tibial insert 100B does not include a post on the central body 106. The shape of the tibial inserts 100A, 100B can be any suitable shape for orthopaedic applications. The tibial inserts 100A, 100B may be formed by, for example, molding from a single material, such as ultra-high molecular weight polyethylene (UHMWPE).

To reduce the risk of abnormal bone loading and corresponding bone abnormalities, each of the tibial inserts 100A, 100B has been modified so the load distribution of implants including the tibial inserts 100A, 100B on surrounding bone tissue simulates natural bone loading when implanted. To do so, as shown, each of the inserts 100A, 100B has one or more stiffness-modifying features 120 defined in or on the central body 106, 116. In the illustrative embodiments of FIGS. 1A and 1B, the stiffness-modifying features 120 are embodied as grooves 122, 132 formed in the central body 106, 116 of the tibial inserts 100A, 100B, respectively.

For example, as shown in FIG. 1A, the tibial insert 100A includes a pair of inner walls 124 that each define a corresponding groove 122, which illustratively extends from an anterior side 126 to a posterior side 128 of the tibial insert 100A. The grooves 122 are defined in the central body 106 of the tibial insert 100A on either side of the post 108. Similarly, as shown in FIG. 1B, the tibial insert 100B includes a pair inner walls 134 that each define a corresponding groove 132, which illustratively extends from an anterior side 136 to a posterior side 138 of the tibial insert 100B. It should be appreciated that although each of the tibial inserts 100A, 100B is illustrated as including two grooves 122, 132, respectively, the tibial inserts 100A, 100B may include additional or fewer grooves in other embodiments.

The formed grooves 122, 132 reduce the stiffness of the tibial inserts 100A, 100B adjacent to the grooves 122, 132, due to the lack of supporting material. As such, the inserts 100A, 100B are less stiff in regions around the grooves. While the stiffness-modifying features 120 are illustrated as grooves in FIGS. 1A and 1B, the stiffness-modifying features 120 may be embodied as other types of modifications, as will be described further herein. The depth, thickness, length, and number of the grooves 122, 132 can be controlled or selected such that the tibial inserts 100A, 100B display a stiffness that simulates natural bone loading after implantation. That is, the stiffness of the tibial inserts 100A, 100B is reduced, relative to a typical tibial insert, such that loading from the patient's surrounding anatomy (e.g., the femur) is transferred to the underlying tibial bone, which generally promotes bone growth. A location and shape of the groove(s) 122, 132 can be chosen such that the grooves 122, 132 are formed in locations at which, for example, the tibial insert 100A, 100B would be overly stiff due to material thickness; the formed groove(s) 122, 132 can reduce the stiffness of the insert 100A, 100B in the overly stiff region by removing material to reduce the risk of stress shielding and other abnormal bone loading.

Figure 2A:
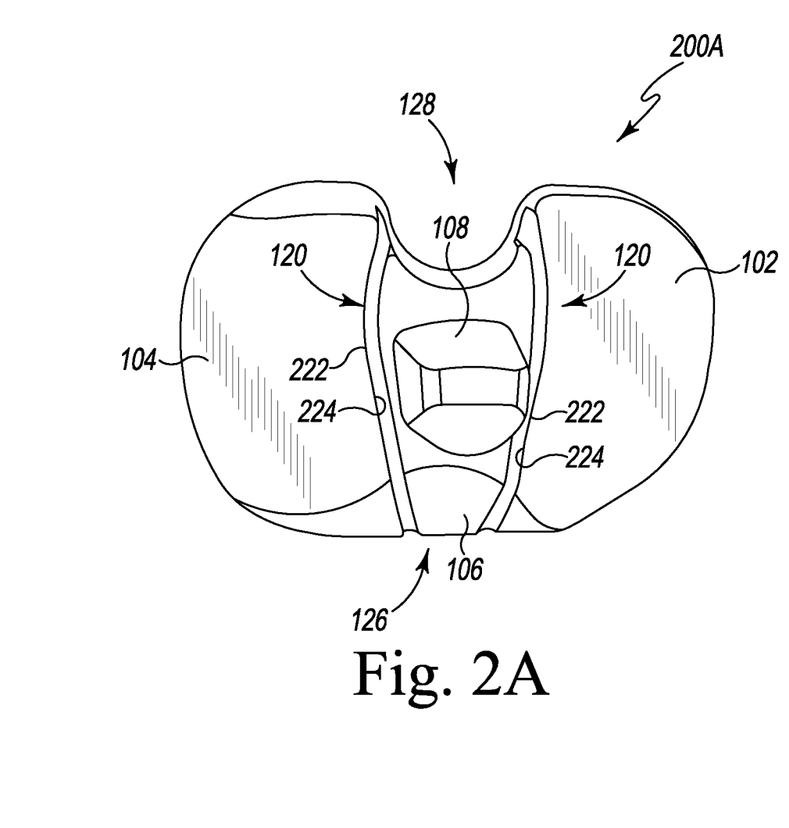
FIG. 2A is a superior plan view of a tibial insert, similar to the tibial insert of FIG. 1A, and having different stress-modifying features defined in a top surface of a body of the tibial insert.
Figure 2B:
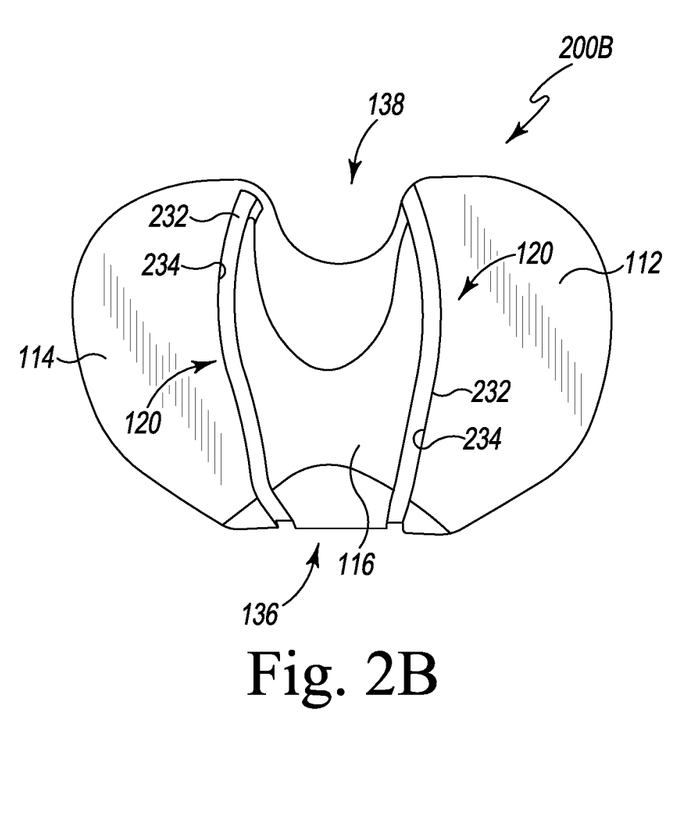
FIG. 2B is a superior plan view of a tibial insert, similar to the tibial insert of FIG. 1B, and having different stress-modifying features defined in a top surface of a body of the tibial insert.

In the illustrative embodiments of FIGS. 1A and 1B, the groves 122, 132 are embodied as straight or linear grooves (e.g., when the tibial inserts 100A, 100B are viewed in a transverse plane) that extend from the anterior side 126, 136 to the posterior side 128, 138 of the corresponding tibial insert 100A, 100B. However, in other embodiments, the stiffness-modifying features 120 may be embodied as curved or non-linear grooves, when the corresponding tibial insert is viewed in a transverse plane. For example, as shown in FIGS. 2A and 2B, tibial inserts 200A, 200B as shown and include stiffness-modifying features 120 embodied as curved or non-linear grooves 222, 232 defined in the central body 106, 116 of the respective tibial insert 200A, 200B. For example, as shown in FIG. 2A, the tibial insert 200A includes a pair of inner walls 224 that define corresponding curved grooves 222 in the central body 106 such that the curved grooves 222 curve around the post 108, which extends upwardly from the central body 106 as discussed above with regard to tibial insert 100A. Similarly, as shown in FIG. 2B, the tibial insert 200B includes a pair of inner walls 234 that define corresponding curved grooves 232 in the central body 116.

Similar to the grooves 122, 132, the curved grooves 222, 232 are formed and located to adjust the stiffness of the tibial inserts 200A, 200B and bone loading characteristics following implantation. Although shown in FIGS. 1A and 1B as having a general arcuate shape, it should be appreciated that the curved grooves 222, 232 may have complex curved shapes in other embodiments to adjust the stiffness of the corresponding tibial insert 200A, 220B in particular areas.

It should be appreciated that the stiffness-modifying features 120 may be embodied as other types of features and included in other tibial implants and/or orthopaedic prostheses. For example, in other embodiments, an illustrative tibial implant may include a tibial insert and a base. In some embodiments, the tibial insert comprises a polymer, such as UHMWPE, that is minimally porous and the base comprises a porous metal, such as titanium, or a porous polymer, such as polyether ether ketone (PEEK), that is at least 30-70% porous. Such a tibial insert may be molded onto the base so the material of the tibial insert infiltrates pores of the base portion to bond the two portions together.

Similar to the tibial inserts described above, the illustrative tibial insert may include a medial articular surface, a lateral articular surface, a central body defined between the medial and lateral articular surfaces, and a post that extends upwardly (i.e., superiorly) from the central body. The illustrative tibial implant may additionally include multiple types of stiffness-modifying features 120 formed in the tibial insert. For example, the illustrative tibial insert may include stiffness-modifying features 120 embodied as a pair of grooves defined in the central body, which may be similar to the grooves described above. Each of the grooves is defined in the central body 316 on opposing sides of the post and extend from an anterior side of the tibial insert to a posterior side of the tibial insert. In the illustrative embodiment, the grooves 322 are linear when the tibial insert is viewed in a transverse plan, but may be curved in the transverse plane in other embodiments.

The illustrative tibial insert also includes a stiffness-modifying feature 120 embodied as a passageway defined in the central body. Illustratively, the passageway is embodied as a blind passageway having an opening defined the anterior side of the tibial insert. However, in other embodiments, the passageway may be embodied as a full passageway having an opening on the anterior side and an opposite opening on the posterior side. Regardless, it should be appreciated that the passageway also modifies the stiffness of the tibial implant by removing material from a region where the tibial insert may be overly stiff. The shape, volume, and location of the passageway can be adjusted to provide the illustrative tibial implant with the desired stiffness.

In some embodiments, a therapeutic agent may be placed in one or more of the stiffness-modifying features 120 (e.g., in a groove and/or the passageway). As used herein, a "therapeutic agent" is a biologically active substance that may have a therapeutic effect when implanted. Exemplary therapeutic agents include, but are not limited to, anti-inflammatories, antimicrobials, cells, growth factors such as bone morphogenetic proteins (BMP), and analgesics. The therapeutic agent may be provided in a therapeutic agent carrier, which can act as a reservoir of the therapeutic agent. The therapeutic agent carrier may be, for example, a sponge, gel, liquid, polymer, or other type of material that holds the therapeutic agent therein for release, which may be immediate or gradual, into surrounding tissue after implantation. The therapeutic agent carrier may have any shape that can be placed in the slot and release therapeutic agent.

In another illustrative embodiment, a tibial implant may include a tibial insert and a base. The illustrative tibial insert and the base may be substantially similar to the previously-described tibial insert and base. For example, the illustrative tibial insert may include a medial articular surface, a lateral articular surface, and a central body defined between the medial and lateral articular surfaces, but does not include the previously-described post. The illustrative tibial implant also includes multiple types of stiffness-modifying features 120 formed in the tibial insert. For example, the illustrative tibial implant includes stiffness-modifying features 120 embodied as a groove and a passageway defined in the central body. The groove is defined in a top surface of the central body and is in fluid communication with, or otherwise connected to, the passageway. In such embodiments, the groove and the passageway may cooperate to form tabs of the central body, which may be moved or pressed inwardly into the passageway via a force applied to the central body.

In some embodiments, a therapeutic agent within a therapeutic agent carrier may be placed in one or more of the stiffness-modifying features 120 (e.g., in the groove and/or the passageway). In some embodiments, the illustrative tibial insert is configured such that high loads exerted on the tibial implant cause compression of the therapeutic agent carrier located in the stiffness-modifying feature 120 (e.g., the passageway) to release the therapeutic agent into surrounding tissues. For example, compressive loads on material adjacent to the groove may force the tabs inwardly into the passageway to compress the therapeutic agent carrier and release therapeutic agent. Such a configuration may, for example, reduce pain and inflammation associated with large impacts.

Figure 3:
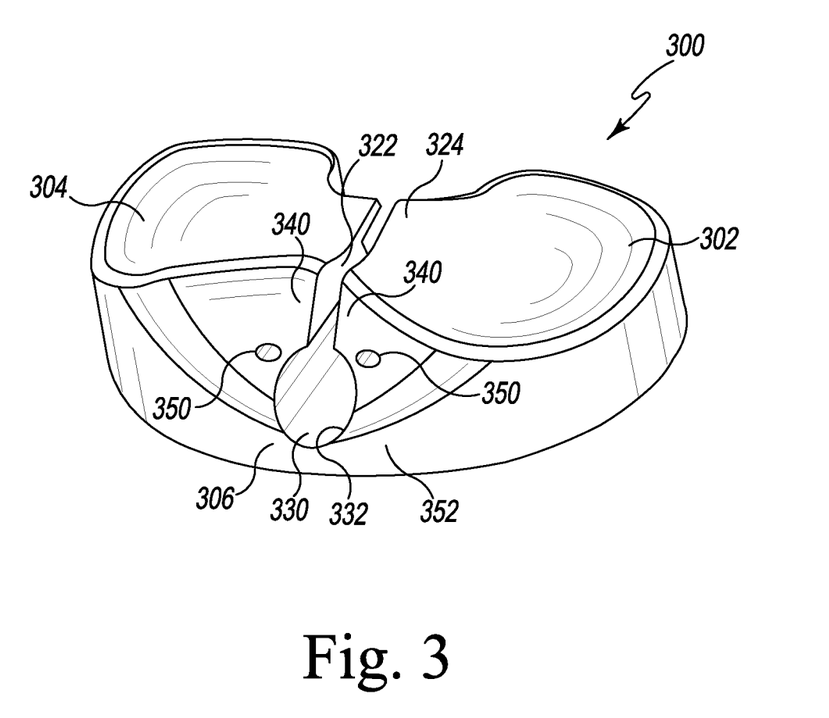
FIG. 3 is a perspective superior view of another embodiment of a tibial insert having stress-modifying features defined therein.

Referring now to FIG. 3, another illustrative embodiment of tibial insert 300 for a tibial implant provided in accordance with the present disclosure is illustrated. The tibial insert 300 is illustratively similar to the previously-described tibial insert. For example, the tibial insert 300 illustratively includes a medial articular surface 302, a lateral articular surface 304, and a central body 306 defined between the medial and lateral articular surfaces 302, 304. Additionally, the tibial insert 300 includes multiple types of stiffness-modifying features 120 formed in the central body 506, including a groove 322 and a passageway 330 defined in the central body 306. The groove 322 is defined in a top surface 324 of the central body 306 and is in fluid communication with, or otherwise connected to, the passageway 330. The groove 322 and passageway 330 cooperate to form tabs 340 of the central body 306, which are movable or compressible into the passageway 330 via a suitable force applied to the central body 306.

The tibial insert 300 may also include a therapeutic agent carrier positioned in the passageway 330 and a therapeutic agent stored in the therapeutic agent carrier. The tibial insert 300 also includes a pair of openings 350 located on an anterior side 352 of the central body 306. Illustratively, the openings 350 are located on a respective side (e.g., a medial and lateral side) of an opening 332 of the passageway 330 defined on the anterior side 352 of the central body 306. Each of the openings 350 may be sized to receive a tensioner, such as a suture. A suture may be passed through the openings 350 and tied to force the tabs 340 together. In other respects, the illustrative tibial insert 300 illustrated in FIG. 3 may be substantially similar to the previously-described tibial inserts.

The previously described tibial inserts and components can be used to form so-called "monolithic" implants that are formed as integral implants. In some instances, a surgeon may wish to use a so-called "modular implant," which has a tibial insert and a tibial base that are mechanically or otherwise interlocked together but separable without destroying either component.

An illustrative embodiment of a tibial base for a modular orthopaedic implant may be formed from, for example, a metal such as cobalt chrome or titanium. The overall stiffness of the illustrative tibial base is partially controlled by the material comprising the tibial base. The illustrative tibial base may also comprise additional features that affect the stiffness, including peripheral rails having a rail thickness, locking features having a locking feature thickness, a cement rail having a cement rail thickness, and a shape of a keel, a stem, and one or more fins. Each of these features may be adjusted to provide the desired stiffness of the tibial base, bearing in mind design constraints such as the overall geometry of the tibial base.

Another illustrative embodiment of a tibial base for a modular orthopaedic implant includes a platform configured for implantation into a surgically-prepared tibia of a patient. The platform includes a rail located about a periphery of the platform. The rail extends superiorly from the platform and, in some embodiments, may be configured to secure or couple with a tibial insert of the modular orthopaedic implant.

The illustrative tibial base includes stiffness-modifying features 120 embodied as slots or recesses formed in various locations to modify the overall stiffness of the tibial base so the formed implant transfers loads to the bone tissue in a manner that simulates natural bone loading. For example, the illustrative tibial base includes slots or recesses formed in the rail. Additionally, the illustrative tibial base includes slots or recesses formed in a top surface of the platform. It should be appreciated that one or more of the described slots may be shaped and sized to receive one or more therapeutic agents, which may or may not be in a therapeutic agent carrier, to elute therapeutic agent(s) following implantation.

Another illustrative embodiment of a tibial base for a modular orthopaedic implant includes a platform configured for implantation into a surgically-prepared tibia of a patient. The platform includes a rail located about a periphery of the platform. The rail extends superiorly from the platform and, in some embodiments, may be configured to secure or couple with a tibial insert of the modular orthopaedic implant.

The illustrative tibial base includes stiffness-modifying features 120 embodied as slots or recesses formed in the rail to adjust the overall stiffness characteristics of the tibial base and formed implant. In some embodiments, one or more of the slots or recesses may be embodied as a section of the rail having a reduced height relative to other sections of the rail.

In yet another illustrative embodiment of a tibial base for a modular orthopaedic implant, the illustrative tibial base may be similar to the previously-described tibial base but include fewer slots formed in a rail located on a periphery of a platform of the illustrative tibial base such that the overall stiffness of the illustrative tibial base is greater than the overall stiffness of the previously-described tibial base.

It should be appreciated that similar tibial bases may differ in where various slots are formed in the corresponding tibial base such that the similarly shaped tibial bases have different overall stiffness characteristics. For example, an illustrative tibial base may include a platform configured for implantation into a surgically-prepared tibia of a patient. The platform includes a rail located about a periphery of the platform. The rail extends superiorly from the platform and, in some embodiments, may be configured to secure or couple with a tibial insert of the modular orthopaedic implant. The illustrative tibial base includes slots or recesses formed in the rail and located so as to adjust the overall stiffness characteristics of the illustrative tibial base and formed implant. Similarly, another tibial base may include a different number of slots formed in a rail located on a periphery of a platform of the other tibial base or formed in different locations of its rail such that the overall stiffness of the other tibial base is different from the prior tibial base.

Figures 4A, 4B, 4C:
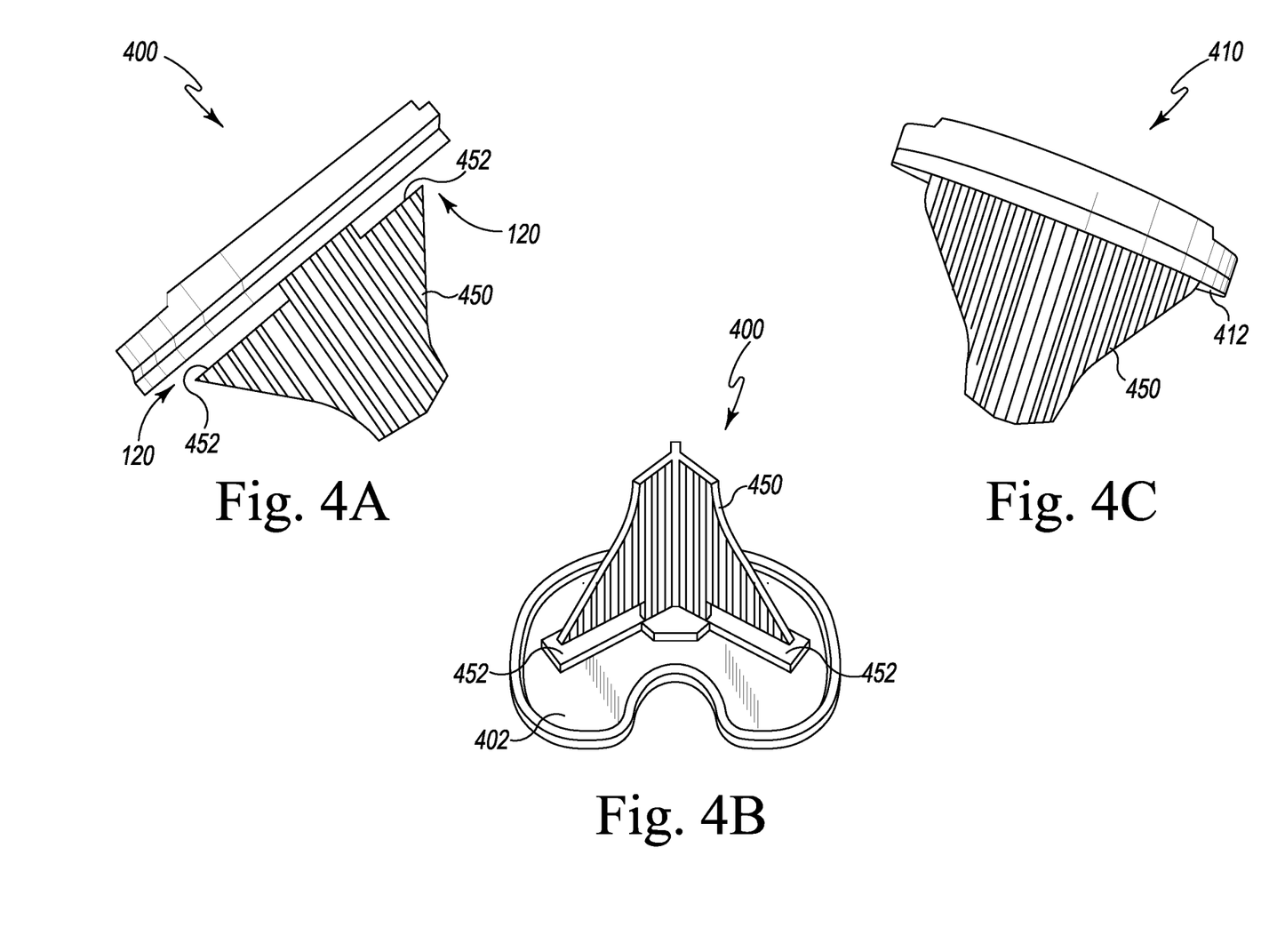
FIG. 4A is an anterior perspective view of a tibial base including a keel having stress-modifying features defined in the keel.
FIG. 4B is a bottom perspective view of the tibial base of FIG. 4A.
FIG. 4C is an anterior perspective view of a known tibial base.

Referring now to FIGS. 4A-4C, another illustrative embodiment of a tibial base 400 for a modular orthopaedic implant provided according to the present disclosure is shown in FIGS. 4A and 4B, with a known tibial base 410 shown in FIG. 4C for comparison. Each of the tibial bases 400, 410 include a fin or keel 450 that extends inferiorly from a bottom surface 402, 412 of the tibial base 400, 402. The tibial base 400, unlike the tibial base 410, has a stiffness-modifying feature 120 in the form of slots or undercuts 452 formed in the fin 450. The slots 452 in the fin 450 can reduce the stiffness behavior of the tibial base 400, and thus the stiffness behavior of an implant incorporating the tibial base 400. The size, location, and number of slots formed in the fins 450 can be adjusted to adjust the overall stiffness characteristics of the tibial base 400.

It should be appreciated that the previously described tibial bases with stiffness-modifying features can be coupled with tibial inserts that also include stiffness-modifying features in order to control the overall stiffness characteristics of a formed implant. Therefore, the overall stiffness characteristics of implants provided according to the present disclosure can be adjusted in many different ways. Illustrative ways of adjusting the overall stiffness characteristics of a tibial base and/or tibial insert, or a monolithic implant, include but are not limited to: selection of metal material and/or treatment for one or more of the components; selection of polymer material and/or treatment for one or more of the components; additive manufacturing to add varying degrees of flexibility in the metal and/or polymer material(s); and introducing slots or other openings with varying locations, orientations, depths, and widths. By adjusting the overall stiffness characteristics of implants to more closely simulate normal bone tissue loading, the risk of abnormal bone growth can be reduced.

Another embodiment of a tibial base may comprise a polymer, such as UHMWPE or PEEK, and have porous metal pads affixed to a bottom surface of the illustrative tibial base. For example, the illustrative tibial base may include multiple (e.g., four) separate porous metal pads attached to the bottom surface that each have a corresponding post. In some embodiments, the illustrative tibial base may include a keel extending inferiorly from the bottom surface. The keel may include a slot that extends superiorly, which splits the keel into two sections (e.g., medial and lateral sections). The slot may further adjust the stiffness of the tibial. Conversely, in another illustrative tibial base, the keel may be solid and not include a slot formed therein. Additionally, the other illustrative tibial base may include a single porous pad attached to the bottom surface. As such, described tibial bases may have different stiffness due to the inclusion of different stiffness-modifying features.

Figure 5:
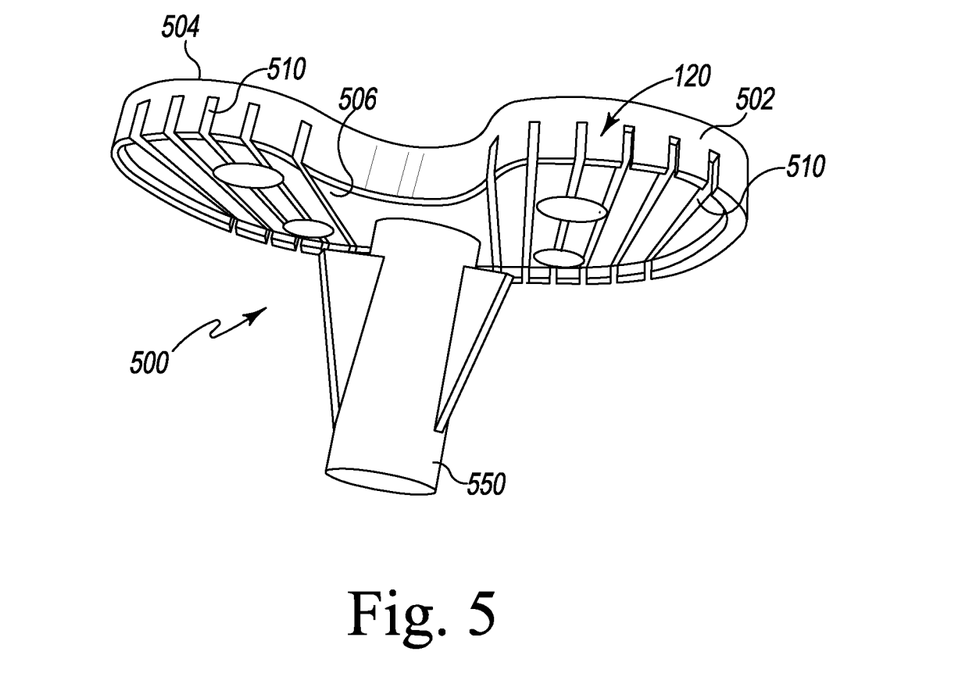
FIG. 5 is an inferior perspective view of a polymer tibial base having stress-modifying features defined on a bottom surface.

Referring now to FIG. 5, another illustrative embodiment of a tibial base 500 provided according to the present disclosure is illustrated. The tibial base 500 may be formed from a polymer, such as UHMWPE or PEEK. The tibial base 500 includes a polymer platform 502 having a superior or top surface 504 and an inferior or bottom surface 506 opposite the superior surface 504, which is configured to rest on a resected tibia after implantation. Additionally, the tibial base 500 may include a keel 550 extending inferiorly from the inferior surface 506 of the polymer platform 502. To modify the stiffness of the tibial base 500, the inferior surface 506 may have several stiffness-modifying features 120 formed therein. For example, as illustrative shown in FIG. 5, the stiffness-modifying features 120 may be embodied as a one or more grooves, slots, or openings 510 defined in the inferior surface 506 of the tibial base 500. The illustrative slots 510 are defined in the inferior surface 506 in an anterior-posterior direction, but may be defined in the inferior surface 506 in other directions in other embodiments. Thus, it should be appreciated that the inferior surface 506 of the tibial base 500 provided according to the present disclosure can also be modified to modify the overall stiffness characteristics of the base portion and the formed implant.

Figure 6:
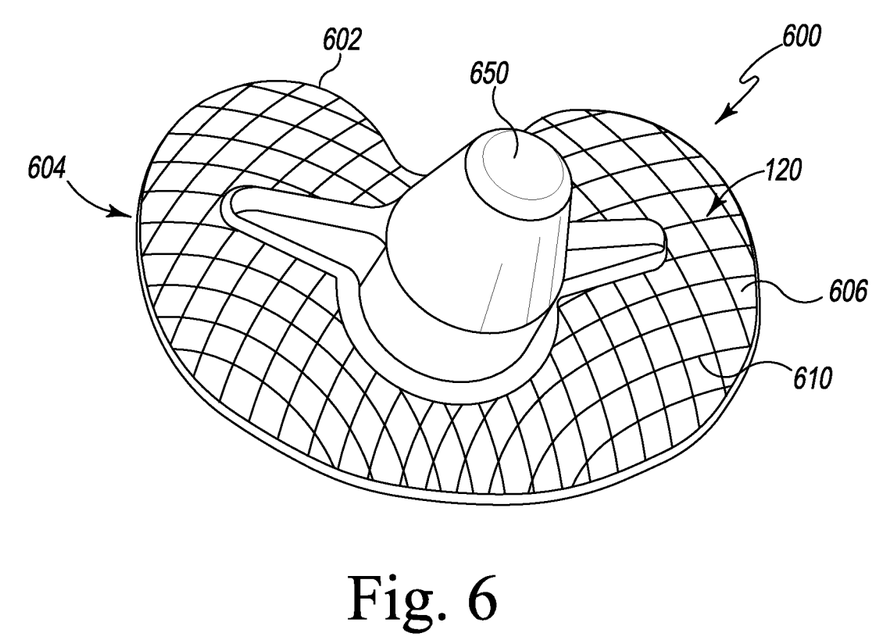
FIG. 6 is an inferior perspective view of another polymer tibial base having stress-modifying features defined on a bottom surface.

Referring now to FIG. 6, another illustrative embodiment of a tibial base 600 provided according to the present disclosure is illustrated. The tibial base 600 may be formed from a polymer, such as UHMWPE or PEEK. The tibial base 600 includes a polymer platform 602 having a superior or top surface 604 and an inferior or bottom surface 606 opposite the superior surface 604, which is configured to rest on a resected tibia after implantation. Additionally, the tibial base 600 may include a keel 650 extending inferiorly from the inferior surface 606 of the polymer platform 602.

The inferior surface 606 is illustratively at least partially covered by a porous ingrowth surface. The porous ingrowth surface may comprise, for example, a porous metal, such as titanium, or polymer, such as PEEK, that has a porous structure to encourage tissue ingrowth into the material to fixate the tibial base 600 to the implantation site. In some embodiments, the porous ingrowth surface has stiffness-modifying features 120, such as slots or grooves 610, formed in the porous material to modify the stiffness of the porous ingrowth surface, and thus the overall stiffness characteristics of the formed implant. Illustratively, the slots 610 are defined in the porous ingrowth surface such that the slots 610 intersect each other to form a "mesh" of slots. Thus, it should be appreciated that the inferior surface 606 of base portions provided according to the present disclosure can have porous ingrowth surfaces with stiffness-modifying features to modify the overall stiffness characteristics of the base portion and the formed implant.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A tibial insert of a tibial implant, the tibial insert comprising:
    a medial articular surface;
    a lateral articular surface; and
    a central body formed between the medial articular surface and the lateral articular surface, wherein the central body includes a stiffness-modifying feature that selectively reduces stiffness of one or more sections of the tibial insert when implanted, wherein the stiffness-modifying feature includes (i) a passageway extending through the central body from an anterior side of the tibial insert to a posterior side of the tibial insert, and (ii) a groove defined on a top surface of the central body from the anterior side of the tibial insert to the posterior side of the tibial insert, wherein the groove is in fluid communication with the passageway, wherein the tibial insert further comprises a therapeutic agent disposed in the passageway.

2. The tibial insert of claim 1, wherein the groove extends linearly from the anterior side of the tibial insert to the posterior side of the tibial insert.

3. The tibial insert of claim 1, wherein the groove curves from the anterior side of the tibial insert to the posterior side of the tibial insert.

4. The tibial insert of claim 1, wherein the passageway is a blind passageway having an opening on an anterior side of the central body or a posterior side of the central body.

5. The tibial insert of claim 1, wherein the passageway includes a first opening on an anterior side of the central body and a second opening on a posterior side of the central body.

6. The tibial insert of claim 1, wherein the groove defines a pair of tabs of the central body, wherein the tabs are movable into the passageway in response to a force applied to the tabs, and wherein the tabs cause a release of the therapeutic agent from the passageway in response to the force.

7. The tibial insert of claim 6, further comprising a pair of openings defined on an anterior side of the central body, each of the openings being configured to receive a tensioner operable to move the tabs of the central body to cause the release of the therapeutic agent from the passageway.

* * * * *